US008268602B2

(12) United States Patent
Raviv et al.

(10) Patent No.: US 8,268,602 B2
(45) Date of Patent: Sep. 18, 2012

(54) CELLULAR AND VIRAL INACTIVATION

(75) Inventors: Yossef Raviv, Rockville, MD (US); Mathias Viard, Frederick, MD (US); Robert Blumenthal, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 1540 days.

(21) Appl. No.: 11/525,250

(22) Filed: Sep. 21, 2006

(65) Prior Publication Data

US 2010/0226938 A1 Sep. 9, 2010

Related U.S. Application Data

(63) Continuation of application No. PCT/US2005/009559, filed on Mar. 22, 2005.

(60) Provisional application No. 60/555,268, filed on Mar. 22, 2004.

(51) Int. Cl.
*C12N 7/01* (2006.01)
*C12N 7/04* (2006.01)

(52) U.S. Cl. .................. 435/173.3; 435/173.7; 435/236; 435/238

(58) Field of Classification Search ........................ None
See application file for complete search history.

(56) References Cited

U.S. PATENT DOCUMENTS

| | | | | |
|---|---|---|---|---|
| 5,232,844 | A * | 8/1993 | Horowitz et al. | 435/173.1 |
| 5,780,287 | A * | 7/1998 | Kraus et al. | 435/236 |
| 6,776,824 | B2 * | 8/2004 | Wen | 96/223 |
| 2009/0297558 | A1 * | 12/2009 | Raviv et al. | 424/209.1 |
| 2011/0038890 | A1 * | 2/2011 | Raviv et al. | 424/204.1 |

FOREIGN PATENT DOCUMENTS

| | | | |
|---|---|---|---|
| WO | WO-9941360 | A1 | 8/1999 |
| WO | WO-2005093049 | A1 | 10/2005 |
| WO | WO-2008054481 | A2 | 5/2008 |

OTHER PUBLICATIONS

Teichert et al. Treatment of oral candidiasis with methylene blue-mediated photodynamic therapy in an immunodeficient murine model. Oral Surgery, Oral Medicine, Oral Pathology, Oral Radiology & Endodontics vol. 93, Issue 2, Feb. 2002, pp. 155-160.*

Chanh et al. Neutralization of HIV-1 and inhibition of HIV-1-induced syncytia by 1,8-naphthalimide photoactive compound. AIDS Res Hum Retroviruses. Sep. 1993;9(9):891-6.*

Nitzan et al. Effect of Photoactivated Hematoporphyrin Derivative on the Viability of *Staphylococcus aureus*. Current Microbiology, vol. 8 (1983), pp. 279-284.*

Abels et al. In vivo kinetics and spectra of 5-aminolaevulinic acid-induced fluorescence in an amelanotic melanoma of the hamster. Br. J. Cancer (1994), 70, 826-833.*

Sausville et al. (Cancer Research, 2006, vol. 66, pp. 3351-3354).*

Johnson et al. (British J. of Cancer, 2001, 84(10):1424-1431).*

"Australian Application Serial No. 2005227320, Office Action Mailed Jan. 6, 2009", 2 pgs.

"Chinese Application Serial No. 200580009241.1, Office Action mailed Jul. 18, 2008", 6 pgs.

"European Application Serial No. 05760441.5, Office Action mailed Jul. 8, 2008", 5 pgs.

"International Application Serial No. PCT/US2005/009559, International Search Report mailed Sep. 12, 2005", 9 pgs.

"International Application Serial No. PCT/US2005/009559, Written Opinion mailed Sep. 12, 2005", 6 pgs.

"International Application Serial No. PCT/US2007/007338, Search Report mailed Aug. 5, 2008", 8 pgs.

"International Application Serial No. PCT/US2007/007338, Written Opinion mailed Aug. 5, 2008", 7 pgs.

Bercovici, T., "5-[125I]Iodonaphthyl Azide, a Reagent to Determine the Penetration of Proteins into the Lipid Bilayer of Biological Membranes", *Biochemistry*, 17(8), (Apr. 18, 1978), 1484-1489.

Chanh, T. C, et al., "Neutralization of HIV-1 and Inhibition of HIV-i-Induced Syncytia by 1, 8-Naphthalinnide Photoactive Compound", *AIDS Res Hum Retroviruses*, 9(9), Mary Ann Liebert, Inc., Publishers, (1993), 891-896.

Chanh, T. C, et al., "Neutralization of HIV-1 and inhibition of HIV-1-induced syncytia by 1,8-naphthalimide photoactive compound", *AIDS Res Hum Retroviruses.*, 9(9), (Sep. 1993), 891-6.

Chanh, T. C, et al., "Photodynamic inactivation of simian immunodeficiency virus", *Journal of Virological Methods*, 26(1), (1989), 125-131.

Gruenert, D. C., et al., "Repair of ultraviolet damage in human cells also exposed to agents that cause strand breaks, crosslinks, monoadducts and alkylations", *Chem Biol Interact.*, 33(2-3), (Jan. 1981), 163-77.

Hanson, C. V, "Rapid Photochemical Inactivation of Human Immunodeficiency Virus HIV", *Journa of Cellular Biochemistry, Supplement #11 Part D, Symposium on Human retroviruses, cancer and aids: Approaches to prevention and therapy.*, (1987), 65.

Merezhinskaya, Natasha, "Reversible penetration of x-glutathione S-transferase into biological membranes revealed by photosensitized labelling in situ", *Biochem J. 335*, (1998), 597-604.

Moreno, G., et al., "Photosensitization of mammalian cells by psoralens and porphyrins", *Biochimie.*, 68(6), (Jun. 1986), 869-73.

Pak, Charles C., et al., "Conformational Changes and Fusion Activity of Vesicular Stomatitis Virus Glycoprotein: [125I]Iodonaphthyl Azide Photolabeling Studies in Biological Membranes", *Biochemistry*, 36(29), (Jul. 22, 1997), 8890-8896.

Pak, Charles C., "Detection of Influenza Hemagglutinin Interaction with Biological Membranes by Photosensitized Activation of [125I]Iodonaphthylazide", *Journal of Biological Chemistry*, 269(20), (May 20, 1994), 14614-14619.

(Continued)

*Primary Examiner* — Zachariah Lucas
*Assistant Examiner* — Michelle S Horning
(74) *Attorney, Agent, or Firm* — Woodcock Washburn LLP

(57) ABSTRACT

The invention provides compositions of inactivated viruses, bacteria, fungi, parasites and tumor cells that can be used as vaccines. Methods for making such inactivated viruses, bacteria, fungi, parasites and tumor cells are also provided.

10 Claims, 6 Drawing Sheets

OTHER PUBLICATIONS

Perlin, M., et al., "Photodynamic Inactivation of Influenza and Herpesviruses by Hematoporphyrin", *Antiviral Research* ,vol. 7,No. 1, (1987), pp. 43-52.
Rai, S, et al., "Dramatic improvements in viral inactivation with brominated psoralens, naphthalenes and anthracenes", *Photochem Photobiol.*, 58(1), (Jul. 1993), 59-65.
Rai, S., et al., "Dramatic improvements in viral inactivation with brominated psoralens, naphthalenes and anthracenes", *Photochemistry and Photobiology*, 58(1), American Society for Photobiology, (1993), 59-65.
Raviv, Y, et al., "Quantitative Measurement of Fusion of HIV-1 and SIV with Cultured Cells Using Photosensitized Labeling", *Virology*, 293 (2), http://www.idealibrary.com, (Feb. 15, 2002), 243-251.
Raviv, Y., "Selective photoinduced uncoupling of the response of adenylate cyclase to gonadotropins by 5-iodonaphthyl 1-azide.", *Biochemistry*, 23(3), (1984), 503-508.
Raviv, Yosef, et al., "Detection of nearest neighbors to specific fluorescently tagged ligands in rod outer segment and lymphocyte plasma membranes by photosensitization of 5-iodonaphthyl 1-azide", *Biochemistry*, 28(3), (Feb. 7, 1989), 1313-1319.
Rossio, J. L, et al., "Inactivation of human immunodeficiency virus type 1 infectivity with preservation of conformational and functional integrity of virion surface proteins", *J Virol.*, 72(10), (Oct. 1998), 7992-8001.
Shao-Chieh, C., et al., "4-Alkylamino-3-Bromo-N-Alkyl-1,8-Naphthalimides; New Photochemically Activatble Antiviral Compounds", *Bioorganic & Medicinal Chemistry Letters*, 3(4), (1993), 555-556.
Snipes, et al., "Inactivation of Lipid-Containing Viruses by Hydrophobic Photosensitizers and Near-Ultraviolet Radiation", *Photochemistry and Photobiology*,Oxford, vol. 29, No. 4, (Jan. 1, 1979), pp. 785-790.
Vzorov, A. N, et al., "Inactivation of human immunodeficiency virus type 1 by porphyrins", *Antimicrob Agents Chemother.*, 46(12), (Dec. 2002), 3917-25.
Wallis, C., et al., "Influenza Vaccine Prepared by Photodynamic Inactivation of Virus", *Journal of Immunology*,vol. 91, (Nov. 1963), pp. 677-682.
Arthur LO, et al., Cellular proteins bound to immunodeficiency viruses: implications for pathogenesis and vaccines. Science. Dec. 18, 1992;258(5090):1935-8.
Arthur LO, et al., Chemical inactivation of retroviral infectivity by targeting nucleocapsid protein zinc fingers: a candidate SIV vaccine. AIDS Res Hum Retroviruses. Oct. 1998;14 Suppl 3:S311-9.
Benveniste et al., Characterization of clones of HIV-1 infected HuT 78 cells defective in gag gene processing and of SIV clones producing large amounts of envelope glycoprotein. J Med Primatol. 1990;19(3-4):351-66.
Berger EA et al., Chemokine receptors as HIV-1 coreceptors: roles in viral entry, tropism, and disease. Annu Rev Immunol. 1999;17:657-700.
Bess JW Jr, et al., Microvesicles are a source of contaminating cellular proteins found in purified HIV-1 preparations. Virology. Mar. 31, 1997;230(1):134-44.
Chan DC, et al., Evidence that a prominent cavity in the coiled coil of HIV type 1 gp41 is an attractive drug target. Proc Natl Acad Sci U S A. Dec. 22, 1998;95(26):15613-7.
Chan DC, et al., HIV entry and its inhibition. Cell. May 29, 1998;93(5):681-4.
Chan DC, et al., Core structure of gp41 from the HIV envelope glycoprotein. Cell. Apr. 18, 1997;89(2):263-73.
Chen CH, et al., A molecular clasp in the human immunodeficiency virus (HIV) type 1 TM protein determines the anti-HIV activity of gp41 derivatives: implication for viral fusion. J Virol. Jun. 1995;69(6):3771-7.
Chen Z, et al., Primary SIVsm isolates use the CCR5 coreceptor from sooty mangabeys naturally infected in west Africa: a comparison of coreceptor usage of primary SIVsm, HIV-2, and SIVmac. Virology. Jun. 20, 1998;246(1):113-24.
Dimitrov DS, Cell biology of virus entry. Cell. Jun. 23, 2000;101(7):697-702.
Dimitrov DS, et al., Kinetics of HIV-1 interactions with sCD4 and CD4+ cells: implications for inhibition of virus infection and initial steps of virus entry into cells. Virology. Apr. 1992;187(2):398-406.
Doms RW, Beyond receptor expression: the influence of receptor conformation, density, and affinity in HIV-1 infection. Virology. Oct. 25, 2000;276(2):229-37.
Düzgünes N, et al., Fusion of HIV-1 and SIVmac with liposomes and modulation of HIV-1 infectivity. Adv Exp Med Biol. 1991;300:167-89.
Frey S, et al., Temperature dependence of cell-cell fusion induced by the envelope glycoprotein of human immunodeficiency virus type 1. J Virol. Mar. 1995;69(3):1462-72.
Furuta RA, et al., Capture of an early fusion-active conformation of HIV-1 gp41. Nat Struct Biol. Apr. 1998;5(4):276-9. Erratum in: Nat Struct Biol Jul. 1998;5(7):612.
Gallo SA, et al., HIV-1 gp41 six-helix bundle formation occurs rapidly after the engagement of gp120 by CXCR4 in the HIV-1 Env-mediated fusion process. Biochemistry. Oct. 16, 2001; 40(41):12231-6.
Hoekstra D, et al., Fluorescence method for measuring the kinetics of fusion between biological membranes. Biochemistry. Nov. 20, 1984;23(24):5675-81.
Hug P, et al., Glycosphingolipids promote entry of a broad range of human immunodeficiency virus type 1 isolates into cell lines expressing CD4, CXCR4, and/or CCR5. J Virol. Jul. 2000; 74(14):6377-85.
Jernigan KM et al., Varying effects of temperature, Ca(2+) and cytochalasin on fusion activity mediated by human immunodeficiency virus type 1 and type 2 glycoproteins. FEBS Lett. Jun. 2, 2000;474(2-3):246-51.
Jiang S, et al., Inhibition of HIV-1 infection by a fusion domain binding peptide from the HIV-1 envelope glycoprotein GP41. Biochem Biophys Res Commun. Sep. 15, 1993;195(2):533-8.
Jonak ZL, et al., A human lymphoid recombinant cell line with functional human immunodeficiency virus type 1 envelope. AIDS Res Hum Retroviruses. Jan. 1993;9(1):23-32.
Kowalski M, et al., Functional regions of the envelope glycoprotein of human immunodeficiency virus type 1. Science. Sep. 11, 1987;237(4820):1351-5.
Krumbiegel M, et al., Kinetics of the low pH-induced conformational changes and fusogenic activity of influenza hemagglutinin. Biophys J. Dec. 1994;67(6):2355-60.
LaCasse RA, et al.,Fusion-competent vaccines: broad neutralization of primary isolates of HIV. Science. Jan. 15, 1999;283(5400):357-62.
Liao Z, et al., Increased infectivity of HIV type 1 particles bound to cell surface and solid-phase ICAM-1 and VCAM-1 through acquired adhesion molecules LFA-1 and VLA-4. AIDS Res Hum Retroviruses. Mar. 1, 2000;16(4):355-66.
Melikyan GB, et al., Evidence that the transition of HIV-1 gp41 into a six-helix bundle, not the bundle configuration, induces membrane fusion. J Cell Biol. Oct. 16, 2000;151(2):413-23.
Merezhinskaya N, et al., Reversible penetration of alpha-glutathione S-transferase into biological membranes revealed by photosensitized labelling in situ. Biochem J. Nov. 1, 1998;335 ( Pt 3):597-604.
Muñoz-Barroso I, et al., Dilation of the human immunodeficiency virus-1 envelope glycoprotein fusion pore revealed by the inhibitory action of a synthetic peptide from gp41. J Cell Biol. Jan. 26, 1998;140(2):315-23.
Ott DE, et al., The majority of cells are superinfected in a cloned cell line that produces high levels of human immunodeficiency virus type 1 strain MN. J Virol. Apr. 1995;69(4):2443-50.
Raviv Y, et al., P-glycoprotein-overexpressing multidrug-resistant cells are resistant to infection by enveloped viruses that enter via the plasma membrane. FASEB J. Mar. 2000;14(3):511-5.
Raviv Y, et al., Photosensitized labeling of a functional multidrug transporter in living drug-resistant tumor cells. J Biol Chem. Mar. 5, 1990;265(7):3975-80.
Raviv Y, et al., Selective labeling of proteins in biological systems by photosensitization of 5-iodonaphthalene-1-azide. Proc Natl Acad Sci U S A. Sep. 1987;84(17):6103-7.
Ugolini S, et al., HIV-1 attachment: another look. Trends Microbiol. Apr. 1999;7(4):144-9.
Volsky, D.J., "Fusion of human immunodeficiency virus type 1 (HIV-1) with human cells as measured by membrane fluorescence dequenching (DQ) method: Roles of HIV-cell fusion in AIDS pathogenesis" In Horizons in Membrane Biotechnology, 1990, Wiley-Liss, New York, pp. 179-198.
Weissenhorn W, et al., Atomic structure of the ectodomain from HIV-1 gp41. Nature. May 22, 1997;387(6631):426-30.
Wild C, et al., A synthetic peptide from HIV-1 gp41 is a potent inhibitor of virus-mediated cell-cell fusion. AIDS Res Hum Retroviruses. Nov. 1993;9(11):1051-3.

* cited by examiner

* = NOT PHOTOACTIVATED

CELLULAR AND VIRAL INACTIVATION

This application is a continuation under 35 U.S.C. 111(a) of PCT/2005/009559, filed Mar. 22, 2005 and published as WO 2005/093049 A1, filed Oct. 6, 2005, which claims benefit of the filing date of U.S. Provisional Application Ser. No. 60/555,268, filed Mar. 22, 2004, which applications and publication are incorporated herein by reference and made a part hereof.

GOVERNMENT FUNDING

The invention described herein was developed with support from the National Cancer Institute. The United States Government has certain rights in the invention.

FIELD OF THE INVENTION

The invention is related to a method for universal inactivation of viruses, parasites and tumor cells. These inactivated agents can be used as vaccines against the diseases caused by such viruses, parasites and tumor cells. The inventive inactivation method preserves the integrity of structural and conformational features of the agent. Hence, the immunogenicity of the agent as a whole is maintained and can be safely used for vaccination without the threat of infection.

BACKGROUND OF THE INVENTION

Vaccination against pathogens has been one of the major accomplishments of medicine over the past century. While effective vaccines have been developed for a large number of diseases, development of safe and effective vaccines for a number of other diseases remains problematic. The use of inactivated or killed microbial agents as a vaccine, although generally safe, will not always be effective if the immunogenic characteristics of the agent are altered. Indeed, the preferential degradation of certain antigens on the inactivated microorganisms might produce a weak or poorly targeted immune response that permits a pathological response when the host is later challenged with the live microorganism. On the other hand, while the preparation of live attenuated microbial agents as vaccines will often provide improved immunologic reactivity, use of such live attenuated microbial agents has an increased risk that the vaccine itself will be infectious. Such live attenuated vaccines can be infectious, for example, as a result of reversion, or the organism may be able to propagate and provide a reservoir for future infection.

Thus, one must generally choose between improved effectiveness and greater degree of safety when selecting between the viral inactivation and viral attenuation techniques for vaccine preparation. The choice is particularly difficult when the virus is resistant to inactivation and requires highly rigorous inactivation conditions that are likely to degrade the antigenic characteristics.

It is therefore desirable to provide improved methods for inactivating agents such as viruses, bacteria, cancer cells and other cell types, where the methods are capable of inactivating these agents without causing substantial degradation of the antigenic structure of the agents. In particular, the inactivated agents should be useful as vaccines and free from adverse side effects at the time of administration as well as upon subsequent challenge with the live agent.

SUMMARY OF THE INVENTION

The invention provides methods for inactivating an infective agent or cancer cell that involve exposing the agent or cell to a hydrophobic photoactivatable compound, for example, 1,5-iodonaphthylazide (INA). These photoactivatable compounds are non-toxic, hydrophobic compounds that penetrate into the innermost regions of biological membrane bilayers and selectively accumulate in such inner membrane regions. Upon irradiation with light, a reactive derivative of the compound is generated that binds to membrane proteins deep in the lipid bilayer. This process specifically inactivates integral membrane proteins embedded in the membrane while maintaining the structural integrity and activity of the proteins that protrude from the extracellular surface of the membrane. Such inactivation is so successful that the inactivated infective agent, cancer cell or other agent of interest, can be used as a vaccine.

DETAILED DESCRIPTION OF THE INVENTION

Figure 1:
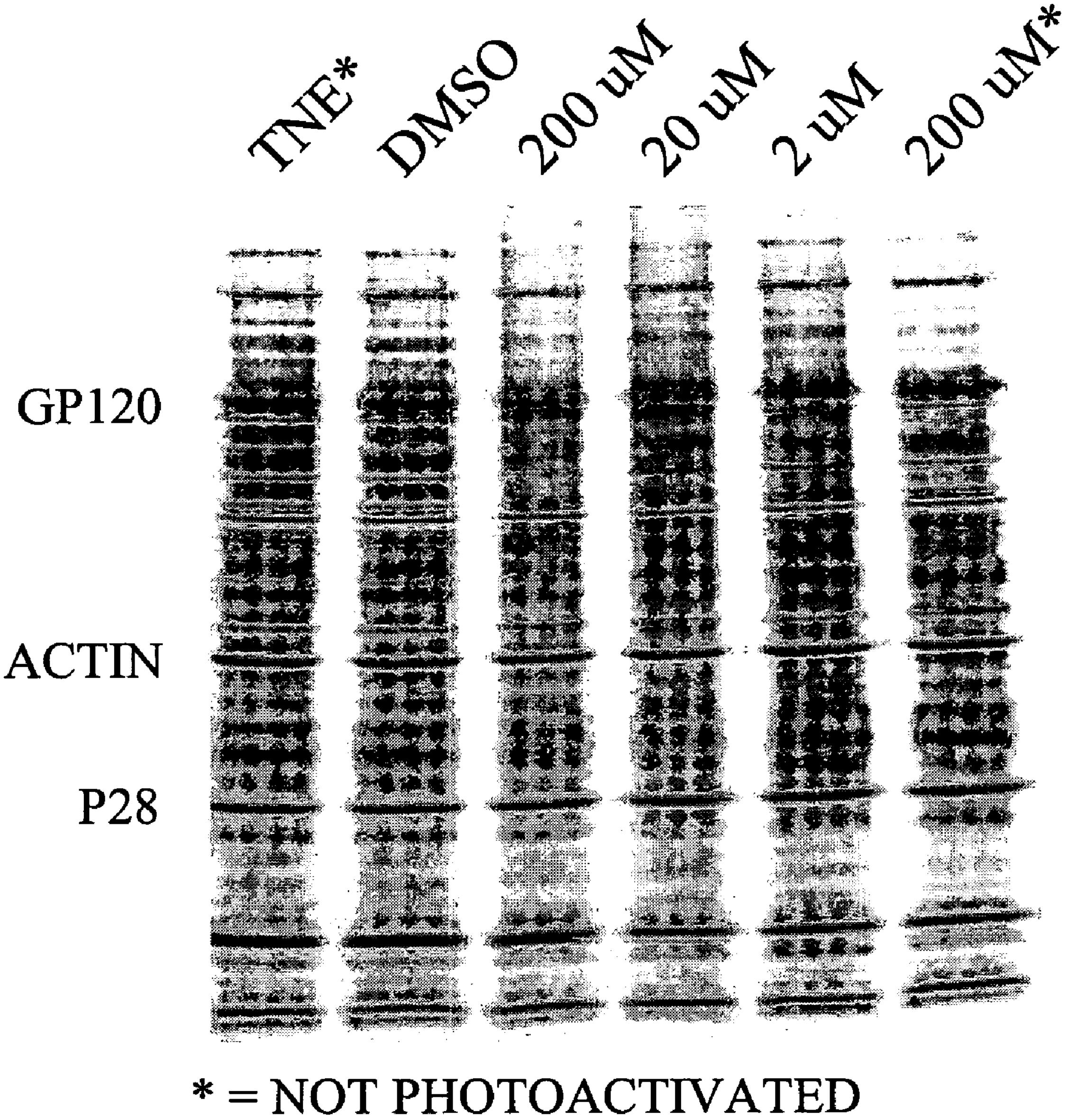
FIG. 1 illustrates that the integrity of SIV proteins was substantially unaffected by INA treatment. The integrity of the virus after the INA treatment was evaluated by recovery of the virus in the pellet using standard procedures for centrifugation of virus and by identifying the major viral proteins in the pellet by SDS-PAGE. Similar results were obtained with INA treated HIV (not shown).

According to the invention, treatment of tumor cells with a photoactivatable hydrophobic compound of the invention blocks cell division and colony formation with substantially no detectable damage to the structural integrity of the cells. Moreover, when live HIV, SIV and Ebola viral particles are treated with appropriate concentration of such photoactivatable hydrophobic compounds, substantially no infectivity is observed. Minor, generally insubstantial changes in the structural integrity of virus particles were observed. These modified viral particles reacted with monoclonal antibodies directed against selected viral proteins and the inactivated viruses bound to their target cells. However, viral fusion with the membrane was impaired by use of the present inventive methods.

Hence, the invention provides new methods for inactivating viruses, bacteria, parasites and tumor cells. These inactivated agents can be used in compositions to stimulate an immune response against active viruses, bacteria, parasites and tumor cells. In another embodiment, the invention provides vaccines to prevent the diseases caused by such viruses, bacteria, parasites and tumor cells.

Photoactivatable Hydrophobic Compounds

Accordingly, as provided herein, a photoactivatable hydrophobic compound of the following formula (I) can be used to inactivate viruses, parasites and tumor cells.

$$X—Ar—Y \qquad \text{I}$$

wherein:

Ar is a hydrophobic moiety; and

X and Y are each independently hydrogen or a reactive group, provided that at least one of X or Y is a reactive group.

The Ar hydrophobic moiety can be any moiety that preferentially partitions out of an aqueous environment and into a cellular or viral membrane. Examples of Ar hydrophobic moieties include linear, branched, cyclic and acyclic hydrocarbons and combinations thereof. The cyclic groups employed can be non-aromatic or aromatic ring moieties. For example, the Ar hydrophobic moiety can be a fatty acid, alkyl, adamantane, phenyl, naphthyl, anthracene, pyrene, phenanthracene or similar moiety.

The X and Y reactive groups are functional groups that are chemically reactive (or that can be made or activated to be chemically reactive) with functional groups typically found in biological materials, or with functional groups that can be readily converted to chemically reactive groups using methods well known in the art. In one embodiment of the invention, the X and/or Y reactive groups are separately azido (—$N_3$), halo (Cl, Br or I), halo lower alkyl (e.g. $CF_3$), diazirene, azidocarbonyloxy (—O—CO—$N_3$), haloacetamide (—NH—(C═O)—$CH_2$—Z), where Z is Cl, Br or I. Alternatively, the reactive groups are separately amine, maleimide, isocyanato (—N═C═O), isothiocyanato (—N═C═S), acyl halide, succinimidyl ester, or sulfosuccinimidyl ester. In another embodiment, the reactive groups are carboxylic acid (COOH), or derivatives of a carboxylic acid. An appropriate derivative of a carboxylic acid includes an alkali or alkaline earth metal salt of carboxylic acid. Alternatively, the reactive groups are reactive derivatives of a carboxylic acid (—COOR), where the reactive group R is one that activates the carbonyl group of —COOR toward nucleophilic displacement. In particular, R is any group that activates the carbonyl towards nucleophilic displacement without being incorporated into the final displacement product. Examples of COOR groups include esters of phenol or naphtol that are further substituted by at least one strong electron withdrawing group, or carboxylic acid activated by carbodiimide, or constitute acyl chloride, azido, succinimidyl or sulfosuccinimidyl ester. Additional charged groups include, among others, sulfonyl halides, sulfonyl azides, alcohols, thiols, semicarbazides, hydrazines or hydroxylamines.

Examples of photoactivatable hydrophobic compounds that can be used in the invention include the following compounds:

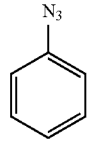

azidobenzene

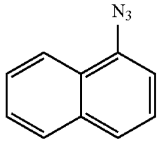

1-azidonaphthalene

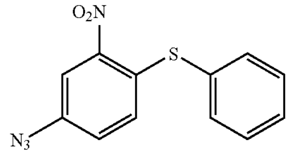

4-azido-2-nitro-1-(phenylthio)benzene

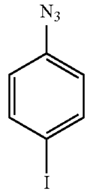

1-azido-4-iodobenzene

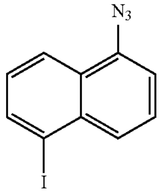

1-azido-5-iodonaphthalene

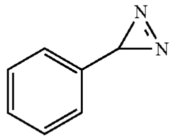

3-phenyl-3H-diazirene

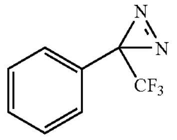

3-phenyl-3-(trifluoromethyl)-3H-diazirene

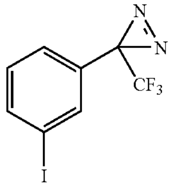

3-(3-iodophenyl)-3-(trifluoromethyl)-3H-diazirene

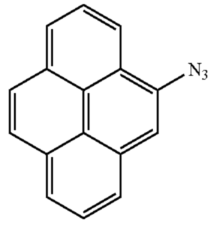

1-azidopyrene

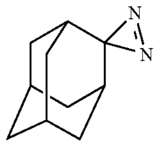

adamantanediazirene

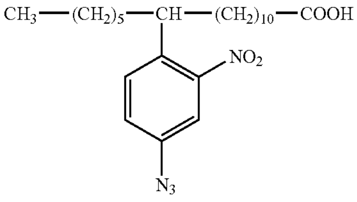

12-(4-azido-2-nitrophenoxy)-stearic acid

-continued

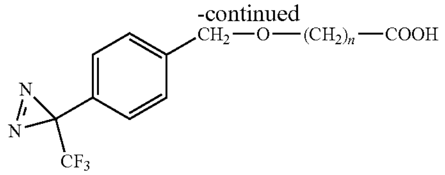

n = 8-15
w-(m-diazirinophenoxy)fatty acids

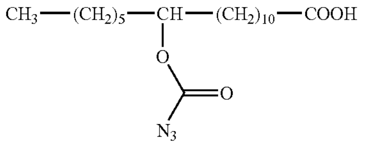

12[(azidocarbonyl)oxy]stearic acid

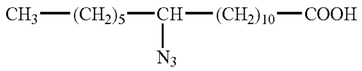

12-azidostearic acid

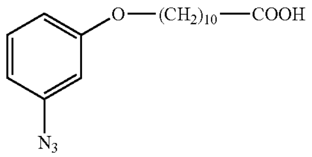

11-(3-azidophenoxy)undecanoic acid

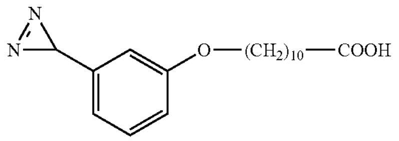

w-(m-diazirinophenoxy)undecanoic acid

In one embodiment, 1,5-iodonaphthyl azide (INA) is employed as a photoactivatable hydrophobic compound. INA is a non toxic hydrophobic compound. The structure for 1,5-iodonaphthyl azide (INA) is provided below. See also, Bercovici and Gitler 1978, Biochemistry, 17: 1484-89.

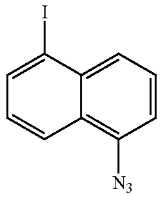

Upon exposure to cells, photoactivatable hydrophobic compounds of the invention will penetrate into the innermost regions of biological membrane bilayers and will accumulate selectively in these regions. Photoactivatable hydrophobic compounds of the invention are also light sensitive. Upon irradiation with ultraviolet light (e.g., 320 to 400 nm) a reactive derivative is generated that binds to membrane proteins deep in the lipid bilayer. This process specifically inactivates integral membrane proteins embedded in the membrane while maintaining the integrity and activity of the proteins that protrude from the extracellular surface of the membrane.

In another embodiment, the photoactivatable hydrophobic compounds of the invention can be used for inactivation of viruses, bacteria, parasites and tumor cells using visible light. However, when visible light is used a photosensitizer chromophore is needed. This photosensitizer chromophore has an absorption maximum in the visible light range and can photosensitize the photoactivatable hydrophobic compounds of the invention. In general, the photosensitizer chromophores have absorption maxima in the range of about 450 to about 525 nm or about 600 to about 700 nm. The photosensitizer chromophore can be a porphyrin, chlorin, bacteriochlorin, purpurin, phthalocyanine, naphthalocyanine, merocyanines, carbocyanine, texaphyrin, non-tetrapyrrole, or other photosensitizer known to one of skill in the art. Specific examples of photosensitizer chromophores include fluorescein, eosin, bodipy, nitro-benzo-diazol (NBD), erythrosine, acridine orange, doxorubicin, rhodamine 123, picoerythrin and the like.

Treatment with Photoactivatable Hydrophobic Compounds

As provided herein, viruses, bacteria, parasites and tumor cells can be inactivated by exposure to photoactivatable hydrophobic compounds. In some embodiments the photoactivatable hydrophobic compound is 1,5-iodonaphthyl azide (INA) or a related compound. After contacting the photoactivatable hydrophobic compound with the virus, parasite or tumor cell to form a mixture thereof, the mixture is exposed to light. If the virus, parasite or tumor cell is contacted with just the photoactivatable hydrophobic compound, ultraviolet light is used. If the virus, parasite or tumor cell is contacted with both the photoactivatable hydrophobic compound and a photosensitizer chromophore that absorbs visible light, then visible light can be used instead. Exposure to ultraviolet light directly photoactivates the photoactivatable hydrophobic compound within viral and cellular membranes. Exposure to visible light first photoactivates the photosensitizer chromophore, which then activates or photosensitizes the photoactivatable hydrophobic compound within viral or cellular membranes. In either case, a reactive derivative of the photoactivatable hydrophobic compound is generated that binds to membrane proteins deep within the lipid bilayer. This process causes specific inactivation of integral membrane proteins embedded in the membrane, while maintaining the integrity and activity of proteins that protrude outside of the membrane.

Prior to exposure to a photoactivatable hydrophobic compound, the viruses, parasites or tumor cells can be washed to remove media, waste and other materials that might reduce partitioning of the photoactivatable hydrophobic compound into viral or cellular membranes. For example, the viruses, parasites or tumor cells can be washed in serum-free media, phosphate-buffered saline or other solutions selected by one of skill in the art.

The amount of photoactivatable hydrophobic compound used to inactivate a virus, bacteria, parasite or tumor cell can vary and may depend upon the type of virus, bacteria, parasite or tumor cell as well as the conditions under which the photoactivatable hydrophobic compound is reacted with the virus, bacteria, parasite or tumor cell. For example, if competing hydrophobic molecules are present in the media, then larger amounts of the photoactivatable hydrophobic compound may be needed.

In some embodiments, the concentration of photoactivatable hydrophobic compound employed in a mixture with a virus, parasite or tumor can vary from about 0.1 micromolar to about 1 millimolar, or from about 1 micromolar to about 700 micromolar, or from about 10 micromolar to about 500 micromolar, or from about 20 micromolar to about 400 micromolar, or from about 50 micromolar to about 300 micromolar, or from about 100 micromolar to about 250 micromolar.

When expressed as a ratio of the amount of photoactivatable hydrophobic compound employed per amount of viral, parasite or tumor protein, this ratio can vary from about 0.1 micrograms photoactivatable hydrophobic compound per milligram of viral, parasite or tumor protein to about 500 micrograms photoactivatable hydrophobic compound per milligram of viral, parasite or tumor protein. In other embodiments, the amount of photoactivatable hydrophobic compound used can vary from about 0.5 to about 200, or about 1 to about 150, or about 2 to about 125, or about 3 to about 100 micrograms photoactivatable hydrophobic compound per milligram of viral, parasite or tumor protein.

The amount of photosensitizer chromophore used to activate the photoactivatable hydrophobic compound can also vary and depends to some extent on the photosensitizer chromophore used, the photoactivatable hydrophobic compound employed and the type of virus, bacteria, parasite or tumor cell. For example, about 0.01 mg/ml to about 50 mg/ml photosensitizer chromophore can be used, or about 0.1 mg/ml to about 5 mg/ml photosensitizer chromophore can be used, or about 0.3 mg/ml to about 1 mg/ml photosensitizer chromophore can be used.

After forming a mixture of the virus, bacteria, parasite or tumor cell with a photoactivatable hydrophobic compound, the mixture is exposed to light for a time and under conditions sufficient for generating a reactive hydrophobic derivative that can bind to membrane proteins within the lipid bilayer. The ultraviolet light employed when only the photoactivatable hydrophobic compound is present has a wavelength that is generally above that absorbed by proteins and nucleic acids. Such a wavelength of ultraviolet light does not cause substantial damage to such proteins and nucleic acids. Thus, for example, the wavelength can be about 320 nm to about 400 nm. In some embodiments, the wavelength is about 330 nm to about 380 nm. In other embodiments, the wavelength is about 340 nm to about 360 nm.

Visible light of an appropriate wavelength can be used when a photosensitizer chromophore is employed that is incubated with or is localized in the vicinity of the hydrophobic photoactivatable compound. In general, the photosensitizer chromophores have absorption maxima in the range of about 450 to about 525 nm or about 600 to about 700 nm.

Light for photoactivation of the photosensitizer chromophore or the hydrophobic derivative can be from various light sources. For example, suitable light sources include broadband conventional light sources, broad arrays of LEDs, laser beams, defocused laser beams, optical fiber devices and transillumination. The light can be filtered to eliminate certain types or wavelengths of light. Hence, the light can be filtered to provide ultraviolet light (e.g., 320 to 400 nm), or visible light of selected wavelengths (e.g., 450 to 525 nm or 600 to 700 nm). The light can also be filtered to reduce heat production, for example, by passing the light through water.

Different light sources of different powers can be used: An incandescent light source like tungsten or halogen lamps will have a power range from 100-200 Watt. Mercury or Xenon light sources have a power range between 100-1000 Watt. A laser source will have the power range of 1-10 Watts. When visible light is used in the presence of a photosensitizer chromophore, the tungsten, halogen, Mercury and Xenon light sources should be equipped with optical filters or a monochromator that will filter out all wavelengths below 400 nm. When a laser is used, the appropriate wavelength line of 400 nm or higher should be used depending on the photosensitizer chromophore employed. Regardless of the light source the intensities of light on the target sample should be in the range of 1-50 milliwatt/cm$^2$/min depending on the nature of the sample and the area irradiated.

Light exposure times can vary. For example, one of skill in the art may choose to expose a mixture of a photosensitizer chromophore and/or a photoactivatable hydrophobic compound with a virus, bacteria, parasite or tumor cell to a light source for about 1 second to about 20 minutes, or about 3 seconds to about 15 minutes, or about 5 seconds to about 10 minutes, or about 7 seconds to about 7 minutes, or about 30 seconds to about 5 minutes. A series of short (e.g., about 1 to about 60 seconds) or longer (e.g., about 20 to about 60 seconds) light exposures can also be employed. When a laser is used, substantially shorter exposure times are typically used, for example, about 0.1 second to about 5 seconds, or about 0.5 seconds to about 3 seconds.

As is appreciated by one of skill in the art, the exposure time can vary depending on the wattage of the light employed. Either cultures or plates of viruses, bacteria, parasites or tumor cells can be treated with a selected photoactivatable hydrophobic compound and/or a photosensitizer chromophore and then exposed to light. The exposure time and wattage of the light employed may be different if a culture or plate of viruses/cells is employed. For example, less exposure may be needed for plated viruses/cells than for viruses/cells cultured in suspension because the depth of the culture may influence the degree to which the light penetrates the culture. Hence, some variation and deviation from the ranges provided herein is possible without deviating from the scope of the invention.

As described in more detail herein, INA has been shown by the inventors to penetrate into the inner most segments of membrane bilayers and accumulate selectively in this domain. As shown herein, upon irradiation of the organism or cell with ultraviolet light (e.g., 320-400 nm), INA is photoactivated in the membrane to generate a reactive derivative that binds to membrane proteins deep within the lipid bilayer. This process causes specific inactivation of integral membrane proteins embedded in the membrane, while maintaining the integrity and activity of proteins that protrude outside the membrane (Raviv et al, 1984 Biochemistry, 23, 503-508).

Methods of Using the Inactivated Microbes, Parasites and Tumor Cells

The invention provides a method that can universally inactivate viruses, bacteria, parasites and tumor cells in a way that they can be safely used as immunological compositions or vaccines to inhibit the disease they cause. The inactivation kills the organism or cell in a specific manner that maintains its structure and conformation. Hence, the structure of the inactivated virus/cell is similar to that of the live virus/cell. In this way, the immunogenicity of the organism or cell as a whole is maintained and can be safely used to stimulate the immune system of a subject animal or patient. Similarly, the inactivated viruses, bacteria, cancer cells or parasites of the invention can be used for vaccination without causing disease or other negative side effects.

A study conducted by the inventors showed that INA treatment of tumor cells blocked their ability to divide and form colonies, with no detectable damage to the structural integrity of the cells.

Figure 2:
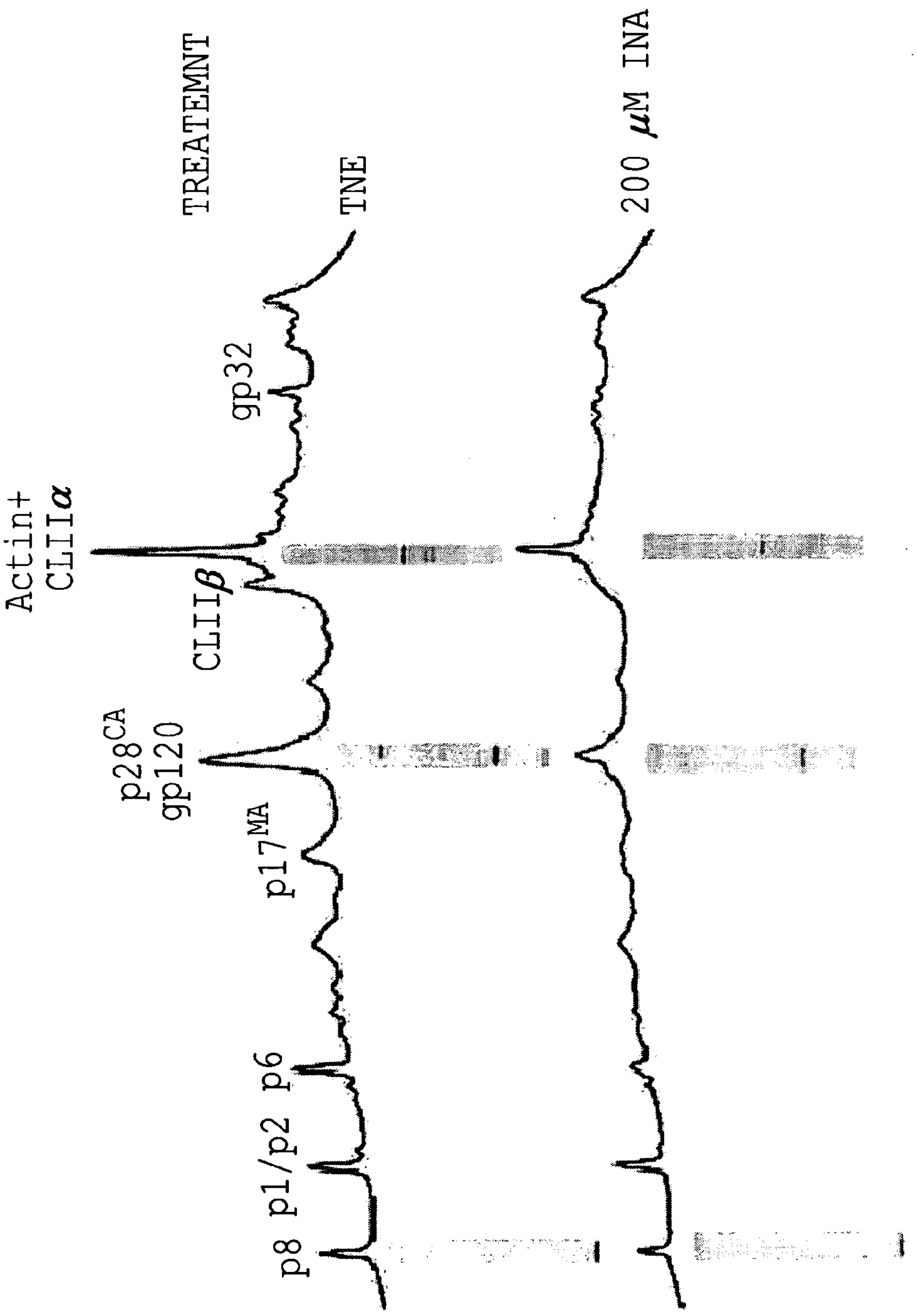
FIG. 2 shows that all detected viral proteins in INA-treated viruses were modified to some extent by INA as measured by their migration patterns on a reverse phase HPLC column. Hence, while the molecular masses of INA-treated viral proteins as observed by SDS-PAGE in FIG. 1 were not changed, some chemical modifications could be observed with HPLC.
Figure 3:
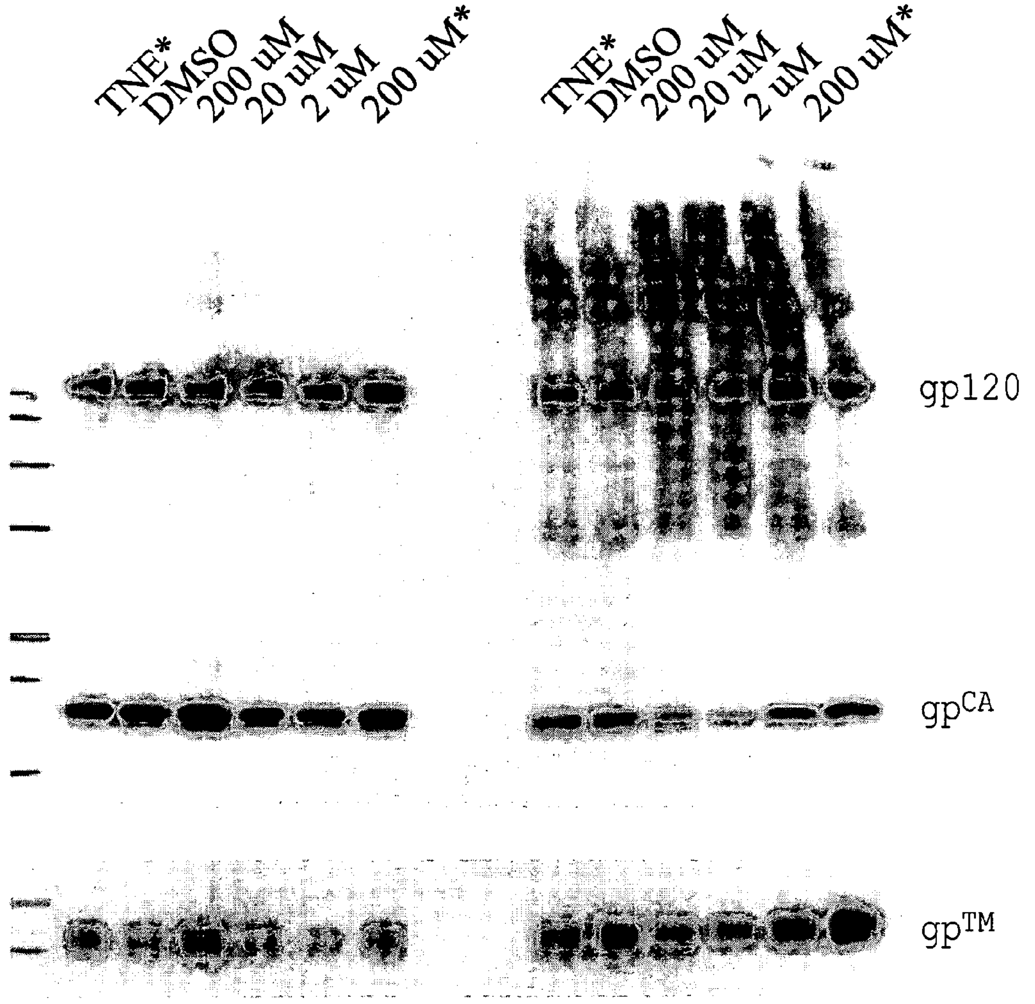
FIG. 3 shows that viral proteins from INA treated virus were still recognized by monoclonal antibodies as revealed by western blot analysis under reducing (R) and non-reducing (NR) conditions.
Figure 4:
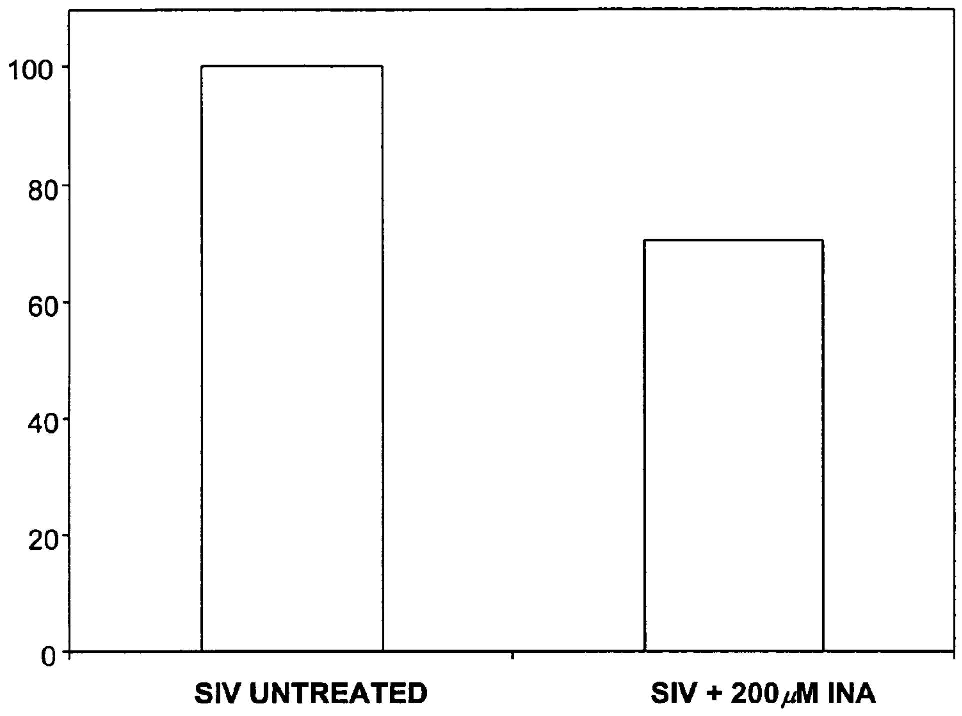
FIG. 4 shows that treatment of SIV with 200 μM INA, which completely inactivated the SN (see Table 1), decreased CD4-independent binding of SIV to target cells by only 30%. Binding was measured by incubation of the virus with cells at room temperature. The cells were washed to remove unbound virus and the amount of gp32 that remained attached to the cells was measured by western blot analysis. CD4 dependent binding was not determined.
Figure 5:
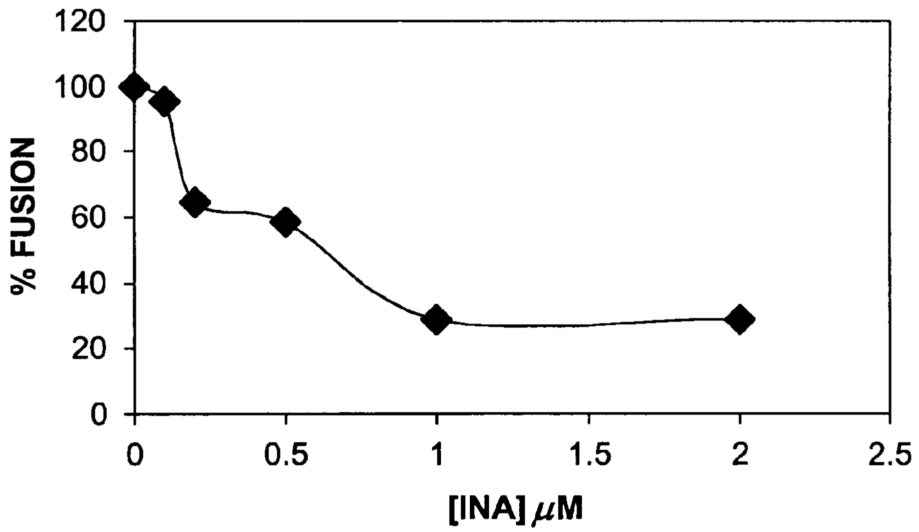
FIG. 5 illustrates that INA treatment blocks fusion of SIV with the target cell at the plasma membrane level, as measured by a photosensitized labeling method developed by the inventors. See Raviv et al. (2002) Virology, 293, 243-251.
Figure 6:
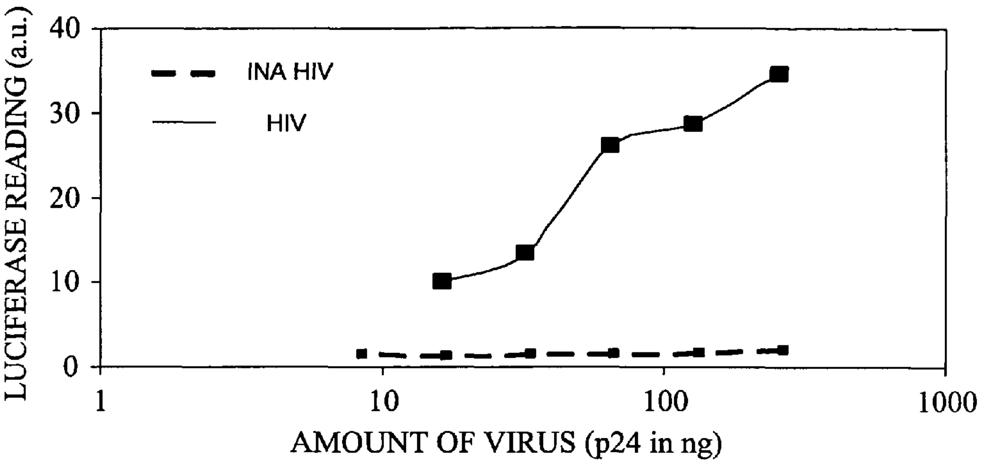
FIG. 6 illustrates the effect of INA treatment on HIV infectivity as measured by a luciferase reporter gene assay. As illustrated, WA-treated HIV exhibit essentially no transcription from viral promoters within the HIV LTR. These results further confirm that the MA-treated viruses used to generate the results in FIG. 1 were indeed inactivated.
Figure 7:
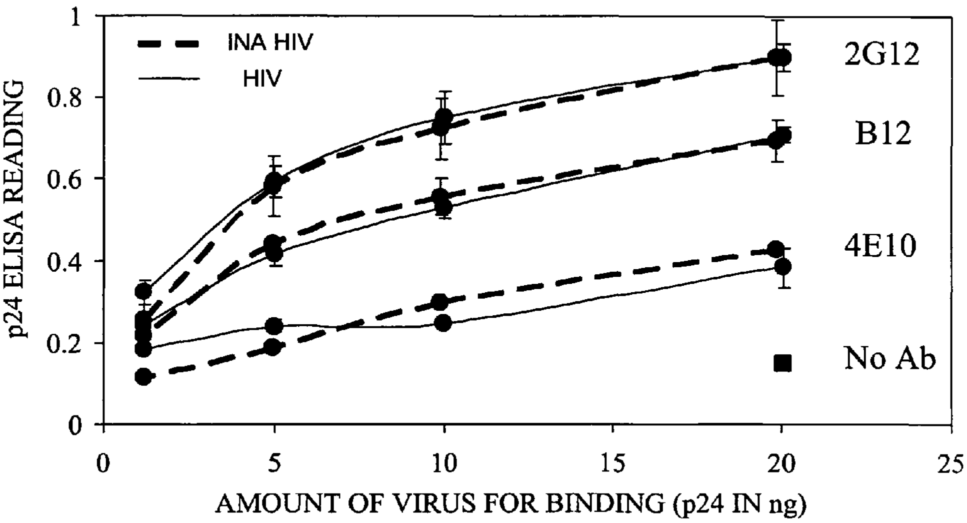
FIG. 7 illustrates that MA-treatment of HIV causes substantially no change in the epitopes recognized by three anti-HIV neutralizing antibody preparations. The antibody preparations tested were the 2G12, B12 and 4E10 antibody preparations. As shown, the amount of virus bound by the three antibody preparations did not change when HIV was treated with INA (dashed lines) as compared to untreated HIV (solid lines).

Studies by the inventors show that INA can also be used to inactivate live HIV, SIV and Ebola viruses. In particular, INA treatment produced inactive viruses with no detectable infectivity (Table 1 and FIG. 6) and with no significant change to their structural integrity (FIGS. 1, 3 and 4). Minor modifications to viral proteins were detected (FIG. 2). However, these modifications did not affect the ability of these proteins to react with antibodies that are known to bind to SIV or HIV (FIGS. 3 and 7). Likewise, the inactive virus was not significantly impaired in its ability to bind to target cells, with the highest concentration of INA (0.2 mM) only reducing the binding by 30% (FIG. 4). However, the INA treatment impaired the ability of the virus to fuse with the target cell at the plasma membrane level (FIG. 5) and to express virally encoded functions (FIG. 6). Viral growth in cells that normally would become infected was essentially eliminated.

Hence, the INA treatment procedures of the invention generate inactive viruses that can be used in a manner similar to aldrithiol inactivated HIV (developed by the AIDS vaccine program SAIC). Alternatively, the INA-inactivation procedures of the invention can be used in conjunction with aldrithiol inactivation procedures to generate inactive HIV that comply with the requirements of the FDA. Thus, two mechanistically independent methods of inactivation can be used to provide a prophylactic AIDS or HIV vaccine.

The present invention is therefore directed to methods of treating or preventing or otherwise ameliorating microbial or parasitic infections in a mammal, as well as other animals, such as farm animals and birds. In another embodiment, the invention provides to methods of treating or preventing or otherwise ameliorating cancer in a mammal, as well as other animals, such as farm animals and birds. These methods include administering to the animal an effective amount, for example, a therapeutically effective amount of an inactivated agent of the present invention, wherein the agent may cause an infection or cancer when not inactivated as described herein.

Prevention or treatment of microbial infections, parasitic infections or cancer is intended to include the alleviation of or diminishment of at least one symptom typically associated with the infection or cancer. Prevention or treatment also includes alleviation or diminishment of more than one symptom. Ideally, treatment with the inactivated agents of the invention generates immunity in the animal towards the agent while prevention by the inactivated agents of the invention substantially eliminates the symptoms associated with the infection or cancer.

Microbial infections that can be treated by the present inactivated agents include infections by any target microbial organisms that can infect a mammal or other animal. Such target microbial organisms include essentially any virus, bacterium, fungus, single cell organism or parasite that can infect an animal, including mammals. For example, target microbial organisms include viruses, bacteria, fungi, yeast strains and other single cell organisms. In another embodiment, the inactivated agents of the invention can give rise to immunity against both gram-negative and gram-positive bacteria.

Treatment of, or prevention of, viral, bacterial, fungal, microbial or parasitic infections is intended to include the alleviation of or diminishment of at least one symptom typically associated with the infection. The treatment also includes alleviation or diminishment of more than one symptom. The treatment may cure the infection, e.g., it may substantially prevent the infection and/or eliminate the symptoms associated with the infection.

Exemplary viral infections that can be treated by the present inactivated agents include infections by any virus that can infect animals (including but not limited to mammals), including enveloped and non-enveloped viruses, DNA and RNA viruses, viroids, and prions. Hence, for example, infections or unwanted levels of the following viruses and viral types can be treated, prevented or addressed by the present inactivated agents: human immunodeficiency virus (HIV), simian immunodeficiency virus (SIV), hemorrhagic fever viruses, hepatitis A virus, hepatitis B virus, hepatitis C virus, poxviruses, herpes viruses, adenoviruses, papovaviruses, parvoviruses, reoviruses, orbiviruses, picornaviruses, rotaviruses, alphaviruses, rubiviruses, influenza virus type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filovirus.

Infections or unwanted levels of the following target viruses and viral types that are believed to have potential as biological weapons can be treated, prevented or addressed by the present inactivated agents: hemorrhagic fever viruses (HFVs), Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, Ebola virus, Machupo virus, Smallpox virus, Yellow fever virus, Hantaan virus, Marburg virus, and Tick-borne encephalitis virus.

Similarly, infections or unwanted levels of the following examples of target microbial organisms can be treated, prevented or addressed by the present inactivated agents: *Aeromonas* spp. (including, for example, *Aeromonas hydrophila, Aeromonas caviae* and *Aeromonas* sobria), *Bacillus* spp. (including, for example, *Bacillus cereus, Bacillus anthracis* and *Bacillus thuringiensis*), *Bacteroides* spp. (including, for example, *B. fragilis, B. thetaiotaomicron, B. vulgatus, B. ovatus, B. distasonis, B. uniformis, B. stercoris, B. eggerthii, B. merdae*, and *B. caccae*), *Campylobacter* spp. (including, for example, *Campylobacter jejuni, Campylobacter laridis*, and *Campylobacter hyointestinalis*), *Clostridium* spp. (such as the pathogenic clostridia including all types of *Clostridium botulinum* (including those in Groups I, II, III and IV, and including those that produce botulism A, B, C, D, E, F and G), all types of *Clostridium tetani*, all types of *Clostridium difficile*, and all types of *Clostridium perfringens*), *Ebola* spp. (e.g. EBOV Zaire), *Enterobacter* spp. (including, for example, *Enterobacter aerogenes* (also sometimes referred to as *Klebsiella mobilis*), *Enterobacter agglomerans* (also sometimes referred to as *Pantoea agglomerans*), *Enterobacter amnigenus, Enterobacter asburiae, Enterobacter cancerogenus* (also sometimes referred to as *Enterobacter taylorae* and/or *Erwinia cancerogena*), *Enterobacter cloacae, Enterobacter cowanii, Enterobacter dissolvens* (also sometimes referred to as *Erwinia dissolvens*), *Enterobacter gergoviae, Enterobacter hormaechei, Enterobacter intermedium, Enterobacter intermedius* (also sometimes referred to as *Enterobacter intermedium*), *Enterobacter kobei, Enterobacter nimipressuralis* (also sometimes referred to as *Erwinia nimipressuralis*), *Enterobacter sakazakii*, and *Enterobacter taylorae* (also sometimes referred to as *Enterobacter cancerogenus*)), *Enterococcus* spp. (including, for example, Vancomycin Resistant *Enterococcus* (VRE), *Enterococcus faecalis, Enterococcus faecium, Enterococcus durans, Enterococcus gallinarum*, and *Enterococcus casseliflavus*), *Escherichia* spp. (including the enterotoxigenic (ETEC) strains, the enteropathogenic (EPEC) strains, the enterohemorrhagic (EHEC) strain designated *E. coli* O157:H7, and the enteroinvasive (EIEC) strains), *Gastrospirillum* spp. (including, for example, *Gastrospirillum hominis* (also sometimes now referred to as *Helicobacter heilmannii*), *Helicobacter* spp. (including, for example, *Helicobacter pylori* and *Helicobacter hepaticus*), *Klebsiella* spp. (including, for example, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*), *Salmo-*

*nella* spp. (including, for example, *S. typhi* and *S. paratyphi* A, B, and C, *S. enteritidis*, and *S. dublin*), *Shigella* spp. (including, for example, *Shigella sonnei, Shigella boydii, Shigella flexneri*, and *Shigella dysenteriae*), *Staphylococcus* spp. (including, for example, *Staphylococcus aureus*, methicillin-resistant *Staphylococcus aureus* (MRSA), *Staphylococcus saprophyticus* and *Staphylococcus epidermis*), *Streptococcus* ssp. (including Groups A (one species with 40 antigenic types, *Streptococcus pyogenes*), B, C, D (five species (*Streptococcus faecalis, Streptococcus faecium, Streptococcus durans, Streptococcus avium*, and *Streptococcus bovis*)), F, and G, including *Streptococcus pneumoniae*), *Pseudomonas* spp. (including, for example, *Pseudomonas aeruginosa, Pseudomonas maltophilia, Pseudomonas fluorescens, Pseudomonas putida, Pseudomonas cepacia, Pseudomonas stutzeri, Pseudomonas mallei, Pseudomonas pseudomallei* and *Pseudomonas putrefaciens*), *Vibrio* spp. (including, for example, *Vibrio cholera* Serogroup O1 and *Vibrio cholera* Serogroup Non-O1, *Vibrio parahaemolyticus, Vibrio alginolyticus, Vibrio furnissii, Vibrio carchariae, Vibrio hollisae, Vibrio cincinnatiensis, Vibrio metschnikovii, Vibrio damsela, Vibrio mimicus, Vibrio vulnificus*, and *Vibrio fluvialis*), *Yersinia* spp. (including, for example, *Yersinia pestis, Yersinia enterocolitica* and *Yersinia pseudotuberculosis*), *Neisseria, Proteus, Citrobacter, Aerobacter, Providencia, Serratia, Brucella, Francisella tularensis* (also sometimes referred to as *Pasteurella tularensis, Bacillus tularensis, Brucella tularensis*, tularemia, rabbit fever, deerfly fever, Ohara's disease, and/or Francis disease), and the like. Thus, for example, various bacterial infections or unwanted levels of bacteria that can be treated, prevented or addressed by the present inactivated agents include but are not limited to those associated with anthrax (*Bacillus anthracis*), *staph* infections (*Staphylococcus aureus*), typhus (*Salmonella typhi*), food poisoning (*Escherichia coli*, such as O157:H7), bascillary dysentery (*Shigella dysenteria*), pneumonia (*Psuedomonas aerugenosa* and/or *Pseudomonas cepacia*), cholera (*Vibrio cholerae*), ulcers (*Helicobacter pylori*), *Bacillus cereus, Salmonella, Clostridium perfringens, Campylobacter, Listeria monocytogenes, Vibrio parahaemolyticus*, botulism (*Clostridium botulinum*), smallpox (*variola major*), listeriosis (*Listeria monocytogenes*), tularemia (*Francisella tularensis*), plague (*Yersinia pestis*; also sometimes referred to as bubonic plague, pneumonic plague, and/or black death) and others. *E. coli* serotype 0157:H7 has been implicated in the pathogenesis of diarrhea, hemorrhagic colitis, hemolytic uremic syndrome (HUS) and thrombotic thrombocytopenic purpura (TTP). As indicated herein, the inactivated agents of the invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

Fungal infections that can be treated or prevented by the present inactivated agents include infections by fungi that infect a mammal, including *Histoplasma capsulatum, Coccidioides immitis, Cryptococcus neoformans, Candida* ssp. including *Candida albicans, Aspergilli* ssp. including *Aspergillus fumigatus, Sporothrix, Trichophyton* ssp., *Fusarium* ssp., *Tricosporon* ssp., *Pneumocystis carinii*, and *Trichophyton mentagrophytes*. Hence, for example, infections or unwanted levels of target fungi can be treated, prevented or addressed by the present inactivated agents. Such fungi also include fungal pathogens that may have potential for use biological weapons, including *Coccidioides immitis* and *Histoplasma capsulatum*.

Anti-microbial activity can be evaluated against these varieties of microbes (viruses, bacteria, fungi and parasites) using methods available to one of skill in the art. In one embodiment, anti-microbial activity is the amount of the inactivated agent that stimulates an immune response against the microbe. In another embodiment, anti-microbial activity is the amount of the inactivated agent that effectively immunizes a mammal against the microbe.

Treatment of, or treating, cancer is intended to include the alleviation of or diminishment of at least one symptom typically associated with the disease. The treatment also includes alleviation or diminishment of more than one symptom. The treatment may cure the cancer, e.g., it may reduce the number of cancer cells and/or arrest the growth of the cancerous tumor.

Cancers that can be treated by the present inactivated agents include solid mammalian tumors as well as hematological malignancies. Solid mammalian tumors include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society (250 Williams Street NW, Atlanta, GA 30303), or from, e.g., Wilson et al. (1991) Harrison's Principles of Internal Medicine, 12.sup.th Edition, McGraw-Hill, Inc. Both human and veterinary uses are contemplated.

Anti-cancer activity can be evaluated against varieties of cancers using methods available to one of skill in the art. Anti-cancer activity, for example, is determined by identifying the $LD_{100}$ or $ED_{50}$ of an inactivated tumor or cancer cell of the present invention that prevents the growth of a cancer. In one embodiment, anti-cancer activity is the amount of the inactivated agent that effectively immunizes a mammal against that cancer type.

According to the present invention, the inactivated agents provided herein do not have substantial or undesired toxicity or infectivity within the mammalian organism to be treated.

Administration of the Inactivated Agents

The inactivated agents of the invention are administered so as to achieve a reduction in at least one symptom associated with an infection, cancer, tumor or other disease, or a decrease in the amount of antibody associated with the infection, cancer, tumor or other disease.

To achieve the desired effect(s), the inactivated agent, or a combination of inactivated agents, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the inactivated agent chosen, the disease, the weight, the physical condition, the health, the age of the mammal, or whether prevention or treatment is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the inactivated agents of the invention is generally intermittent over a preselected period of time, for example, in a series of spaced doses. Both local and systemic administration is contemplated.

To prepare the composition, inactivated agents are prepared according to the methods described herein, and purified as necessary or desired. In some embodiments the inactivated agents can be lyophilized and/or stabilized. The inactivated agent can then be adjusted to the appropriate concentration, and optionally combined with other agents.

The absolute weight of a given inactivated agent included in a unit dose can vary widely. For example, about 0.01 to about 2 g, or about 0.1 to about 500 mg, of at least one inactivated agent of the invention, or a plurality of inactivated agents, can be administered. Alternatively, the unit dosage can vary from about 0.01 g to about 5 g, from about 0.01 g to about 3.5 g, from about 0.01 g to about 2.5 g, from about 0.1 g to about 1 g, from about 0.1 g to about 0.8 g, from about 0.1 g to about 0.4 g, or from about 0.1 g to about 0.2 g.

One or more suitable unit dosage forms comprising the therapeutic inactivated agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic inactivated agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic inactivated agents of the invention are prepared for oral administration, they are generally combined with a pharmaceutically acceptable carrier, diluent or excipient to form a pharmaceutical formulation, or unit dosage form. For oral administration, the inactivated agents may be present as a powder, a granular formulation, a solution, a suspension, an emulsion or in a natural or synthetic polymer or resin for ingestion of the agents from a chewing gum. The inactivated agents may also be presented as a bolus, electuary or paste. Orally administered therapeutic inactivated agents of the invention can also be formulated for sustained release, e.g., the inactivated agents can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic inactivated agents of the invention can be prepared by procedures known in the art using well-known and readily available ingredients. For example, the inactivated agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the inactivated agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one inactivated agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more inactivated agents of the invention are designed to resist disintegration in the stomach and dissolve in the more neutral to alkaline environment of the duodenum.

The inactivated agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic inactivated agents of the invention can also take the form of an aqueous or anhydrous solution or dispersion, or alternatively the form of an emulsion or suspension or salve.

Thus, the therapeutic inactivated agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The inactivated agents and other ingredients may form suspensions, solutions, or emulsions in oily or aqueous vehicles, and may contain formulatory agents such as suspending, stabilizing and/or dispersing agents. Alternatively, the inactivated agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if desired, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more inactivated agents of the present invention and one or more other anti-microbial agents. For example, a variety of antibiotics can be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the inactivated agents are well suited to formulation as sustained release dosage forms and the like. The formulations can be so constituted that they release the inactivated agent, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the inactivated agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic inactivated agents of the invention can be delivered via patches or bandages for dermal administration. Alternatively, the inactivated agent can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The inactivated agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the inactivated agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic inactivated agent may further be formulated for topical administration in the mouth or throat. For example, the active ingredients may be formulated as a lozenge further comprising a flavored base, for example, sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The inactivated agents of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, cancer, tumor or disease. Any statistically significant attenuation of one or more symptoms of an infection, cancer, tumor or disease that has been treated pursuant to the methods of the present invention is considered to be a treatment or prevention of such infection, cancer, tumor or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197-224, Butterworths, London, England, 1984).

Therapeutic inactivated agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the inactivated agents of the present invention specific for the indication or disease to be treated or prevented. Dry aerosol in the form of finely divided solid inactivated agent that are not dissolved or suspended in a liquid are also useful in the practice of the present invention. Inactivated agents of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating or preventing the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic inactivated agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling microbial infections or cancer such as a kit or other container. The kit or container holds a therapeutically effective amount of a pharmaceutical composition for controlling microbial infections, or cancer or tumor growth and instructions for using the pharmaceutical composition for control of the microbial infection or for control of the cancer or tumor. The pharmaceutical composition includes at least one inactivated agent of the present invention, in a therapeutically effective amount such that microbial infection, cancer or tumor is controlled.

The invention is further illustrated by the following non-limiting Examples.

EXAMPLE 1

Illustrative Materials and Methods

This Example provides many of the reagents and procedures employed for several experiments described herein.

Materials

Antibodies and their sources were as follows: anti-HLA-DR IgG L243 (mAb from Elena Chertova), anti-HLA-DR IgG DA6-147 (mAb from Paul Roche), and anti-Gp32 IgG (rabbit polyclonal Ab from Raoul Benveniste). [$^{125}$I]INA (300 mCi/mmol) was purchased from Lofstrand Laboratories (Gaithersburg, Md.). All other biochemical reagents used were of the highest purity available and were obtained from regular commercial sources.

Viruses

HIV-$1_{MN}$/H9 clone 4 was propagated in H9 cells, as described previously (Ott at al. 1995). SIVmne was obtained from supernatants of the cloned E11 S cell lines derived from a culture of HuT-78 cells infected with SIVmne (Benveniste at al. 1990). Concentrated virus preparations were produced by sucrose gradient banding in a continuous-flow centrifuge (Bess at al. 1997). Inactivation of SIV by treatment with aldrithiol-2 was performed as described (Rossio at al. 1998).

Cell Cultures

Ghost-345 cells (derived from human osteosarcoma cells) that stably express CD4, as well as CXCR4 and CCR5, and NIH3T3 CD4/X4 were obtained from Dan Littman and Vineet KewalRamani. TF228 cells derived from the BJAB human B cell line and that stably express the HIV-$1_{LAI}$ envelope glycoprotein (Jonak at al. 1993) were from Zdenka L. Jonak (Smith-Kline & Beecham, King of Prussia, Pa.). SupT1 (human CD4-expressing T-Lymphoblastic cell line) and TF228 were grown in RPMI supplemented with 10% fetal bovine serum (FBS) (Life Technologies, Inc., Rockville). NIH3T3 CD4 cells were grown in Dulbecco's modified Eagle's medium+10% FBS (D10). NIH3T3 CD4/X4 cells were grown in D10+3 mg/ml puromycin. Ghost 345 cells were grown in D10+500 mg/ml G418+100 mg/ml hygromycin+1 mg/ml puromycin. All the cells were grown in the presence of penicillin and streptomycin.

Treatment with INA

Viruses or cells were suspended in Phosphate Buffered saline (PBS) at a concentration of 0.5-1.0 mg/ml. A stock solution of 30 mM NA in DMSO was prepared. INA was added to the cell or viral suspension under dim light to a final concentration of 1-200 μM. The INA was added so that the total DMSO will not exceed 1% of the total sample volume. Addition of INA was done in installments of 3-4 aliquots while mixing vigorously after each aliquot. The sample was incubated at room temperature for 30 minutes and washed once in PBS.

The suspension was then irradiated with an ozone free 100 W mercury arc lamp and through a water filter to eliminate heat and a 320 nm cut-off filter. Time of irradiation vary with the size of the sample. For a 1 ml sample and a cross-area of 1 cm$^2$ the irradiation time was 2 minutes. For a 20 ml sample and a cross area of 10 cm$^2$ the irradiation time was 5 minutes.

Labeling of the Target Cells

The fluorescent lipid DiO (Molecular Probes, Eugene, OR) was diluted in 50% Diluent C (SIGMA-ALDRICH, St. Louis, MO) and 50% serum-free RPMI (RPMI) to a final concentration of 50 mM. After two washes in RPMI the cells were incubated in the DiO solution for 30 min at room temperature. They were then washed once with clear RPMI and further incubated 30 min in medium at room temperature. They were then washed three times with PBS, in which they were finally resuspended. At this point [$^{125}$I]INA(1 Ci/mmol) was added in the amount of 10 mCi for each experimental group. Upon 20 min incubation in the dark, the cells were washed with PBS and subsequently used for the photolabeling experiment.

Measurement of Fusion by Photo-Sensitized Labeling

The HLA-DR$^+$ virions are incubated with the HLA-DR$^-$ target cells labeled with the fluorescent lipid analog 3,3'-dioctadecyloxacarbocyanine (DiO) and [$^{125}$I]INA for binding at room temperature. Plasma membranes of target cells bearing CD4 and coreceptors are labeled with the fluorescent lipid analog 3 dioctadecyloxacarbocyanine (DiO). [$^{125}$I]INA spontaneously partitions from the medium into viral and other target membranes. In the bound state only integral membrane proteins of the DiO-labeled target membranes react with [$^{125}$I]INA following photoactivation by visible light. Upon incubation of virus-cell complexes at 37° C., DiO becomes part of the viral membrane as a result of fusion and therefore photoactivation using visible light results in covalent attachment of [$^{125}$I]INA to viral membrane-resident proteins. At different times following incubation at 37° C., samples are irradiated with visible light, the cells are lysed, and the HIV or SIV Env, as well other viral envelope-resident proteins such as HLA-DR, is isolated from other radioactively labeled proteins by immunoprecipitation. The extent of radioactivity incorporated into these proteins is then a quantitative measure of viral fusion at the plasma membrane level.

In the case of HIV-1, 1 ml virus (0.79 mg/ml capsid) was added to $3\times10^8$ SupT1 cells in 3 ml. In case of SIVmne, 0.2 ml of virus (0.084 mg/ml capsid) was added to 3 ml medium overlaid on attached Ghost-345 cells. The unbound virions were then removed and the samples subjected to fusion at the desired temperature. At defined times cells were irradiated with an argon laser (Lexel Laser, Inc., Freemont, Calif.) in the multiline mode of 488/514 nm. Suspension cells were irradiated horizontally for two consecutive 10-s periods with a beam of 400 mW that was passed through a UV cut-off filter and focused on an area of 1 $cm^2$ (133 $mW/cm^2/min$). Plated cells were irradiated for 60 s vertically using a 5-W beam focused on an area of 144 $cm^2$ (11 $mW/cm^2/min$).

The cells were then collected and lysed (2% Triton X-100 in Tris-buffered saline (TBS; 50 mM Tris, 138 mM NaCl, 2.7 mM KCl, pH 8) containing protease inhibitors) for 2 h at 4° C. The insoluble material was spun down at 15,000 rpm for 15 mM in an Eppendorf microcentrifuge. The supernatant was then diluted twice in TBS and total protein was measured using the BCA protein determination reagent (Pierce, Rockford, Ill.). Samples were subjected to immunoprecipitation using L243 (for HLA-DR) or anti-SIV gp32 for the SIV Env. Upon overnight incubation with the respective antibody, protein G-agarose was added for 2 h and washed five times with TBS containing 1% Triton X-100. Proteins were separated by 14% SDS-PAGE and transferred to nitrocellulose membranes. Blots were incubated for 1 h in PBST (phosphate-buffered saline, 0.2% Tween 20) containing 5% powdered skim milk. Membranes were incubated for 2 h with the primary antibody in a 3% BSA solution containing 0.2% Tween 20 and for 1 h 30 min with a peroxidase-conjugated secondary antibody in PBST. Immunoreactivity was detected by using an ECL kit (Amersham, Piscataway, N.J.) and an imaging system with high dynamic range (Bio-Rad GS 505 Molecular Imager System, Hercules, Calif.). The blots were then exposed to Phosphorimager screens; bands were quantified using a Storm system (Molecular Dynamics Sunnyvale, Calif.) and the Image Quant software (Molecular Dynamics).

HIV-1 Envelope Glycoprotein-mediated Cell-Cell Fusion

For the photo-sensitized labeling experiments HLA-DR+ TF228.1.16 effector cells and DiO-labeled HLA-DR target cells were loaded with [$^{125}$I]INA and incubated for various times at 37° C. The plates were irradiated for 60 s with a 5-W laser beam over an area of 144 $cm^2$ (11 $mW/cm^2/min$) and incorporation of [$^{125}$I]INA into HLA-DR was measured as described above. For the dye redistribution experiments target cells were labeled with the cytoplasmic dye 5- and 6-([(4-chloromethyl)benzoyl]amino) tetramethylrhodamine (CMTMR) at a concentration of 1.5 mM for 1 h at 37° C. Envelope-expressing cells were labeled with calcein AM at a concentration of 1 mM for 1 h at 37° C. Calcein-labeled effector cells were co-cultured with CMTMR-labeled target cells for 2 h at 37° C., and dye redistribution was monitored microscopically as described previously (Munoz-Barroso et al. 1998). The extent of fusion was calculated as:

$$\text{percent fusion} = \frac{100\times\text{number of bound cells positive for both dyes}}{\text{number of bound cells positive for } CMTMR}$$

EXAMPLE 2

INA-Treated SW cannot Fuse with Mammalian Cells

This Example describes the results of experiments showing that INA treatment inactivates viruses but leaves them substantially intact. However, such treatment inhibits viral fusion with host cells and prevents viral infection.

FIG. 1 shows a Coomassie-stained SDS-PAGE gel illustrating that treatment of SIV virions with INA causes insubstantial changes in the molecular weights of viral proteins. As shown, exposure to INA at concentrations ranging from 2 μM to 200 μM caused substantially no change in the separation pattern of SIV proteins as compared to untreated virions (DMSO) and virions that were treated with either THE (0.1 M Tris HCl, 0.1 M NaCl, 1 mM EDTA) or 200 μM INA but not exposed to light. Similar results were obtained when these experiments were repeated with HIV. These results indicate that INA treatment maintains the integrity of the majority of viral proteins.

However, as shown by reverse phase HPLC analysis of viral proteins under reducing conditions (FIG. 2), many viral proteins were modified to some extent by INA. As a result, the migration patterns of these viral proteins on the HPLC column were altered. But even though there are some changes in viral proteins after treatment with INA, several major viral proteins were still recognized by monoclonal antibodies directed against those proteins (FIG. 3). Hence, for example, the GP120, P28 and GP32 proteins from INA-treated virions were recognized by monoclonal antibodies directed against the respective untreated proteins.

When 200 μM INA was used to treat SIV, CD4 independent binding of SIV decreased only by 30% (FIG. 4). Binding was measured by incubation of the virus with cells at room temperature. The cells were washed to remove unbound virus and the amount of gp32 that remained attached to the cells was measured by western blot analysis. CD4 dependent binding was not determined. These results show that SIV can bind to host cells even though the SIV has been treated with INA. These results further illustrate that INA treatment has little effect on the structural integrity and activity of the majority of viral proteins.

However, even though INA-treated virions can bind to host cells, they exhibit reduced fusion with those host cells. As shown by FIG. 5, INA treatment blocked fusion of SIV with the target cell at the plasma membrane level, as measured by a photosensitized labeling method developed by the inventors (see Example 1). Hence, the types of minor structural changes caused by INA treatment appear to be sufficient to undermine the functioning of the viruses.

More significantly, the infectivity of SIV was 100% blocked by treatment with appropriate levels of INA. Table 1 illustrates that INA treatment completely blocks infection of SIV as measured by the expression of the viral protein P-28 at different times after the introduction of the virus. In particular, at 200 μM INA infectivity was blocked by 100%.

TABLE 1

INA Blocks SIV Infectivity

| SAMPLE | SIV P28 (PG/ML) DAY 3 | DAY 7 | DAY 11 |
|---|---|---|---|
| NO Treatment | 5,490 | 156,987 | 179,324 |
| DMSO Treatment | <955 | 71,363 | 94,730 |
| 200 uM INA | <955 | <955 | <955 |
| 20 uM INA | <955 | 1,939 | 32,670 |
| 2 uM INA | <955 | 94,084 | 126,480 |
| 200 uM INA (NO LIGHT) | 4,978 | 124,939 | 200,413 |
| NEg CTRL | <955 | <955 | <955 |

These data indicate that INA treatment gives rise to viral particles that have minor but significant structural changes. The structural changes do not affect the ability of the viral particles to be recognized by antibodies (FIGS. 3 and 7) or bind with host cells (FIG. 4). However, INA treatment does inhibit viral fusion with host cells (FIG. 5). Even more importantly, INA treatment substantially eliminates viral infectivity (Table 1). Hence, INA is a useful reagent for inactivating infectious agents, for example, so that those inactivated infectious agents may be used as vaccines.

EXAMPLE 3

INA-Treated HIV are Transcriptionally Inactive in Mammalian Cells

This Example describes the results of experiments showing that INA treatment inactivates human immunodeficiency viral transcription, thereby illustrating by another procedure that INA treatment inactivates HIV.

Infectivity assay was carried out using the luciferase reporter gene assay, essentially as described in Spenlehauer, C., Gordon, C., Trkola, A. and Moore, J. (2001) Virology 280, 292-300; and Wei, X., Decker, J., Liu, Z., Zhang, Z., Arani, R., Kilby, M., Saag, M., Wu, X., Shaw, G., and Kappes, J. (2002) Antimicrobial Agents and Chemotherapy, 46, 1896-1905.

Briefly, JC53BL cells were used that express the luciferase enzyme under the transcriptional control of HIV long terminal repeat (LTR). Upon HIV infection the TAT protein from the virus binds to the LTR to induce the expression of Luciferase. The level of Luciferase expression can be assessed by incubation of the sample with a luciferase substrate which triggers a chemiluminescent signal that can be easily quantified by a luminometer.

As shown in FIG. 6, substantially no luciferase expression is detected after JC53BL cells were exposed to INA-treated HIV. However, HIV viruses that were not exposed to INA readily induced expression of luciferase.

These results further demonstrate the effectiveness of INA for inactivating HIV. No effective vaccines are currently available for preventing HIV infection. However, the results provided herein indicate that the present compositions involving INA-inactivated HIV may be useful as vaccines.

EXAMPLE 4

INA-Treated HIV Bind to Neutralizing Anti-HIV Antibodies

This Example describes the results of experiments showing that INA treatment does not destroy the antigenicity of HIV. Instead, INA-treated HIV readily binds to available anti-HIV neutralizing antibodies.

The antibodies employed were the 2G12 and B12 antibodies that target Gp120 and the 4E10 antibody that targets gp41. Each of these antibody preparations is broadly neutralizing of HIV infectivity.

Antibody binding to HIV virions was measured by an immunocapture procedure essentially as described in Nyambi, P., Burda, S., Bastani, L., and Williams, C. (2001) Journal of Immunological Methods, 253, 253-262. Briefly, 10 microgram of each antibody was coated onto 96 well ELISA plates and non-specific binding was blocked with BSA. HIV was then added and incubated for binding for one hour at 37° C. using different amounts of virus as indicated in FIG. 7. A control assay was performed in which no antibody was used. After washing, the samples were lysed and analyzed for the presence of virus by measuring the viral protein, p24, using an ELISA assay. Each experimental point was carried out in triplicate.

The results are provided in FIG. 7. As shown, FIG. 7 illustrates that INA-treated HIV interacts substantially the same as the non-treated virus with all three antibody preparations. These antibodies were originally derived from human AIDS patients that developed these antibodies spontaneously. Cells producing these antibody preparations were cloned to generate anti-HIV monoclonal antibody preparations. Each of these human monoclonal antibody preparations specifically recognizes structural epitopes on HIV envelope proteins. The 2G12 and B12 antibodies recognize epitopes on the gp120 protein and the 4E10 antibodies recognize an epitope on the gp41 fusion protein. These three antibody clones are broadly neutralizing, i.e. they block infection by many types of HIV in cell culture assays. Hence, these antibodies probe epitopes on HIV that have the potential of inducing antibodies in humans that will block viral infections.

As illustrated herein, each of these antibodies recognizes and binds to INA-inactivated HIV, demonstrating that the epitopes recognized by the antibodies are substantially unaffected by INA treatment.

EXAMPLE 5

INA-Treated Ebola Viruses Fail to Grow in Mammalian Cells

This Example illustrates that INA inhibits growth of Ebola virus cultured with mammalian cells.

Figure 8:
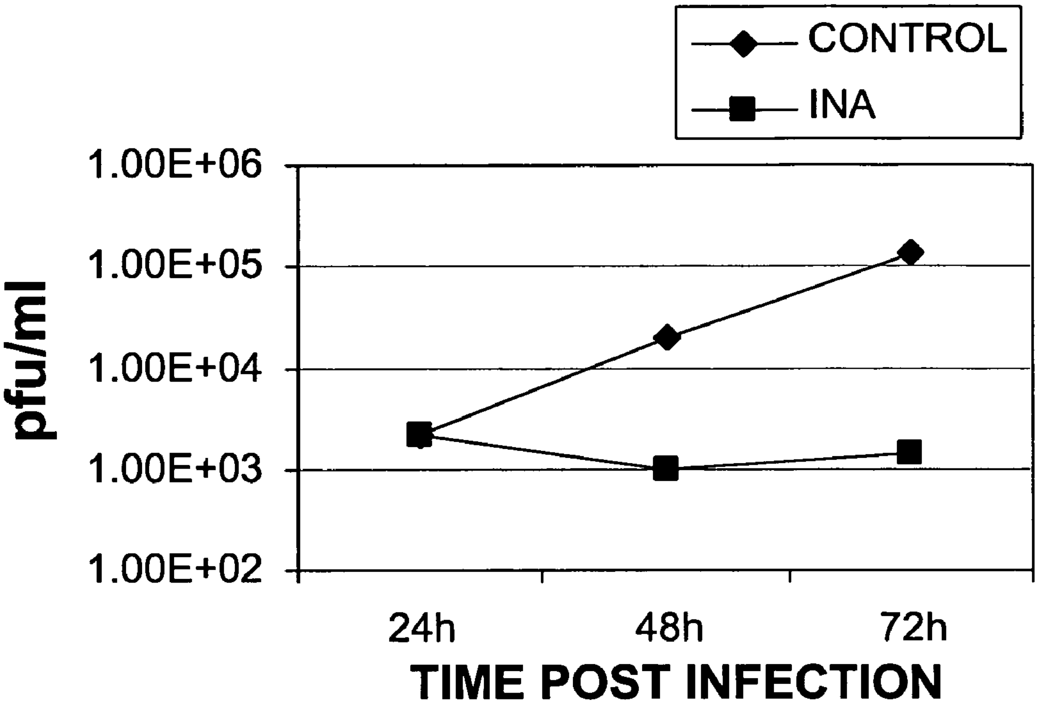
FIG. 8 shows that INA treatment of Ebola viral particles effectively eliminates viral growth in mammalian cells (Vero-E6 cells). Ebola viral particles were incubated with INA or DMSO (Control), exposed to ultraviolet light and then cultured with Vero-E6 cells. At selected time points (shown on the x-axis), aliquots of the virus/cell mixture were removed and the number of viruses (plaque-forming units, pfu) was determined. As shown, control-treated Ebola virus grew well on Vero-E6 cells but INA-treated Ebola virus failed to grow.

The EBOV Zaire strain of Ebola virus was used for these studies. Confluent Vero E6 cells were used to monitor the viral replication. $4\times10^4$ virus particles (PFUs) were treated with 0.1 mM INA or 0.33% DMSO (control) for 30 min at 4° C. in the dark. After adding 20 mM Glutathione (reduced form, pH 7.5), the viral suspensions were exposed to UV light for 10 minutes. The viral suspensions were then added to cells and incubated for 50 minutes at 37° C. to allow attachment. Subsequently, excess virus was washed and medium added. At the time points indicated in FIG. 8, a fraction of the supernatant was removed and lysed in triazole. Viral RNA was prepared and the particle number was assessed by real time PCR. As shown in FIG. 8, INA-treated viral particles failed to grow in Vero-E6 cells.

These data indicate that INA may be an effective inactivation agent for use in preparing immune system-stimulating compositions of hemorrhagic fever viruses such as Ebola virus.

REFERENCES

Arthur et al. (1998). Chemical inactivation of retroviral infectivity by targeting nucleocapsid protein zinc fingers: A candidate SIV vaccine. AIDS Res. Hum. Retroviruses 14(Suppl. 3), S311-S319.

Arthur et al. (1992). Cellular proteins bound to immunodeficiency viruses: Implications for pathogenesis and vaccines. Science 258, 1935-1938.

Benveniste et al. (1990). Characterization of clones of HIV-1 infected HuT 78 cells defective in gag gene processing and of SIV clones producing large amounts of envelope glycoprotein. J. Med. Prima 19, 351-366.

Bercovici, T, and Gitler, C. (1978). [$^{125}$I]Iodonaphthyl azide, a reagent to determine the penetration of proteins into the lipid bilayer of biological membranes. Biochemistry 17: 1484-89.

Berger, E. A, Murphy, P. M., and Farber, J M. (1999). Chemokine receptors as HIV-1 coreceptors: Roles in viral entry, tropism, and disease. Annu. Rev. Immunol., 657-700.

Bess et al. (1997). Microvesicles are a source of contaminating cellular proteins found in purified HIV-1 preparations. Virology 230, 134-144.

Chan, D.C., Chutkowski, C. T, and Kim, P. S. (1998). Evidence that a prominent cavity in the coiled coil of HIV type 1 gp41 is an attractive drug target. Proc. Natl. Acad. Sci. USA 95: 15613-17.

Chan, D. C., Fass, D., Berger, J M., and Kim, P. S. (1997). Core structure of gp41 from the HIV envelope glycoprotein. Cell 89: 263-273.

Chan, D. C., and Kim, P. S. (1998). HIV entry and its inhibition. Cell 93: 681-684.

Chen, C. H., Matthews, T. J., McDanal, C. B., Bolognesi, D. P., and Greenberg, M. L. (1995). A molecular clasp in the human immunodeficiency virus (HIV) type 1 TM protein determines the anti-HIV activity of gp41 derivatives: Implication for viral fusion. J. Viral. 69: 3771-3777.

Chen, Z., Gettie, A, Ho, D. D., and Marx, P. A (1998). Primary SIVsm isolates use the CCR5 coreceptor from sooty mangabeys naturally infected in west Africa: A comparison of coreceptor usage of primary SIVsm, HIV-2, and SIVmac. Virology 246, 113-124.

Dimitrov, D. S. (2000). Cell biology of virus entry. Cell 101, 697-702.

Dimitrov, D. S., Willey, R., Martin, M., and Blumenthal, R. (1992). Kinetics of HIV-1 interactions with sCD4 and CD4+ cells: Implications for inhibition of virus infection and initial steps of virus entry into cells. Virology 187, 398-406.

Doms, R. W (2000). Beyond receptor expression: The influence of receptor conformation, density, and affinity in HIV-1 infection. Virology 276, 229-237.

Duzgunes, N., Larsen, C. E., Konopka, K., Alford, D. R., Young, L. J., McGraw, T. P., Davis, B. R., Nir, S., and Jennings, M. (1991). Fusion of HIV-1 and SIVmac with liposomes and modulation of HIV-1 infectivity. Adv. Exp. Med. Biol. 300, 167-189.

Frey, S., Marsh, M., Gunther, S., Pelchen-Matthews, A, Stephens, P., Ortlepp, S., and Stegmann, T (1995). Temperature dependence of cell-cell fusion induced by the envelope glycoprotein of human immunodeficiency virus type 1. J. Virol., 1462-72.

Furuta, R. A., Wild, C. T, Weng, Y, and Weiss, C. D. (1998). Capture of an early fusion-active conformation of HIV-1 gp41. Nat. Struct. Biol. 5: 276-279.

Gallo, S. A., Puri, A, and Blumenthal, R. (2001). HIV-1 gp41 six-helix bundle formation occurs rapidly after the engagement of gp120 by CXCR4 in the HIV-1 Env-mediated fusion process. Biochemistry 40:12231-12236.

Hoekstra, D., de Boer, T, Klappe, K., and Wilschut, J (1984). Fluorescence method for measuring the kinetics of fusion between biological membranes. Biochemistry 23, 5675-5681.

Hug, P., Lin, H. M., Korte, T, Xiao, X., Dimitrov, D. S., Wang, J M., Puri, and Blumenthal, R. (2000). Glycosphingolipids promote entry of a broad range of human immunodeficiency virus type 1 isolates into cell lines expressing CD4, CXCR4, and/or CCR5. J. Virol., 74: 6377-6385.

Jernigan, K. M, Blumenthal, R., and Puri, A (2000). Varying effects of temperature, Ca(2+) and cytochalasin on fusion activity mediated by human immunodeficiency virus type 1 and type 2 glycoproteins. FEBS Lett. 474, 246-251.

Jiang, S., Lin, K., Strick, N., and Neurath, A R. (1993). Inhibition of HIV-1 infection by a fusion domain binding peptide from the HIV-1 envelope glycoprotein GP41. Biochem. Biophys. Res. Commun. 195, 533-538.

Jonak, Z. L., Clark, R. K., Matour, D., Trulli, S., Craig, R., Henri, E., Lee, E. V., Greig, R., and Debouck, C. (1993). A human lymphoid recombinant cell line with functional human immunodeficiency virus type envelope. AIDS Res. Hum. Retroviruses, 9: 23-32.

Kowalski, M., Potz, J, Basiripour, L., Dorfman, T, Goh, W C., Terwilliger, Dayton, A, Rosen, C., Haseltine, W, and Sodroski, J (1987). Functional regions of the envelope glycoprotein of human immunodeficiency virus type 1. Science 237, 1351-1355.

Krumbiegel, M., Herrmann, A, and Blumenthal, R. (1994). Kinetics of the low-pH induced conformational changes and fusogenic activity of influenza hemagglutinin. Biophys. J. 67, 2355-2360.

LaCasse, R. A, Follis, K. E., Trahey, M., Scarborough, J. D., Littman, D. R., and Nunberg, J H. (1999). Fusion-competent vaccines: Broad neutralization of primary isolates of HIV. Science 283, 357-362.

Liao, Z., Roos, J. W., and Hildreth, J. E. (2000). Increased infectivity of HIV type 1 particles bound to cell surface and solid-phase ICAM-1 and VCAM-1 through acquired adhesion molecules LFA-1 and VLA-4. AIDS Res. Hum. Retroviruses 16, 355-366.

Lifson, J D., Feinberg, M. B., Reyes, G. R., Rabins, L., Banapour, B. Chakrabarti, S., Moss, B., Wong-Staal, F., Steimer, K. S., and Engleman, E. G. (1986). Induction of CD4-dependent cell fusion by the HTLV-III/LAV envelope glycoprotein. Nature 323, 725-728.

Melikyan, G. B., Markosyan, R. M., Hemmati, H., Delmedico, M. K., Lambert, D. M., and Cohen, F. S. (2000). Evidence that the transition of HIV-1 gp41 into a six-helix bundle, not the bundle configuration, induces membrane fusion. J. Cell Biol. 151: 413-423.

Merezhinskaya, N., Kuijpers, G. A, and Raviv, Y. (1998). Reversible penetration of alpha-glutathione S-transferase into biological membranes revealed by photosensitized labeling in situ. Biochem. J. 335, 597-604.

Munoz-Barroso, I., Durell, S., Sakaguchi, K., Appella, E., and Blumenthal, R. (1998). Dilation of the human immunodeficiency virus-1 envelope glycoprotein fusion pore revealed by the inhibitory action of a synthetic peptide from gp41. J. Cell Biol. 140, 315-323.

Ott, D. E., Nigida, S. M., Jr., Henderson, L. E, and Arthur, L. O. (1995). The majority of cells are superinfected in a cloned cell line that produces high levels of human immunodeficiency virus type 1 strain MN. J. Virol. 69, 2443-2450.

Pak, C. C., Krumbiegel, M., Blumenthal, R., and Raviv, Y. (1994). Detection of influenza hemagglutinin interaction with biological membranes by photosensitized activation of [$^{125}$I]Iodonaphthylazide. J. Biol. Chem. 269, 14614-14619.

Pak, C. C., Puri, A., and Blumenthal, R. (1997). Conformational changes and fusion activity of vesicular stomatitis virus glycoprotein: [$^{125}$I]Iodonaphthylazide photo labeling studies in biological membranes. Biochemistry 36, 8890-8896.

Raviv, Y., Bercovici, T. and Salomon, Y. (1984) Biochemistry 23: 503-508.

Raviv, Y., Bercovici, T., Gitler, C., and Salomon, Y. (1989). Detection of nearest neighbors to specific fluorescently tagged ligands in rod outer segment and lymphocyte plasma membranes by photosensitization of 5-iodonaphthyl 1-azide. Biochemistry 28, 1313-1319.

Raviv, Y., Pollard, H. B., Bruggemann, E. P., Pastan, I., and Gottesman, M. M. (1990). Photosensitized labeling of a functional multidrug transporter in living drug-resistant tumor cells. J. Biol. Chem. 265, 3975-3980.

Raviv, Y., Puri, A., and Blumenthal, R. (2000). P-glycoprotein-overexpressing multidrug-resistant cells are resistant to infection by enveloped viruses that enter via the plasma membrane. FASEB J. 14: 511-515.

Raviv, Y., Salomon, Y., Gitler, C., and Bercovici, T. (1987). Selective labeling of proteins in biological systems by photosensitization of iodonaphthalene-1-azide. Proc. Natl. Acad. Sci. USA 84, 6103-6107.

Raviv, Y., Viard, M., Bess Jr., J. and Blumenthal, R. (2002) Virology 293: 243-351.

Rossio, J. L., Esser, M. T, Suryanarayana, K., Schneider, D. K., Bess, J. W., Jr., Vasquez, G. M., Wiltrout, T. A, Chertova, E., Grimes, M. K., Sattentau, Q., Arthur, L. O., Henderson, L. E., and Lifson, J D. (1998). Inactivation of human immunodeficiency virus type 1 infectivity with preservation of conformational and functional integrity of virion surface proteins. J. Virol. 72: 7992-8001.

Ugolini, S., Mondor, I., and Sattentau, Q. J. (1999). HIV-1 attachment: Another look. Trends Microbiol. 7: 144-149.

Volsky, D. J. (1990). Fusion of human immunodeficiency virus type 1 (HIV-1) with human cells as measured by membrane fluorescence dequenching (DQ) method: Roles of HIV—cell fusion in AIDS pathogenesis. In "Horizons in Membrane Biotechnology," pp. 179-198, Wiley-Liss, New York.

Weissenhorn, W., Dessen, A., Harrison, S. C., Skehel, J. J, and Wiley, D. C. (1997). Atomic structure of the ectodomain from HIV-1 gp41. Nature 387, 426-428.

Wild, C., Greenwell, T, and Matthews, T (1993). A synthetic peptide from HIV-1 gp41 is a potent inhibitor of virus-mediated cell-cell fusion. AIDS Res. Hum. Retroviruses 9, 1051-1053.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of inactivating a human immunodeficiency virus, comprising the steps (a) contacting a human immunodeficiency virus with an effective amount of 1,5-iodonaphthyl azide to form a mixture of the human immunodeficiency virus and the 1,5-iodonaphthyl azide, and (b) exposing the mixture to ultraviolet light for a time sufficient to inactivate the human immunodeficiency virus.

2. The method of claim 1, wherein an effective amount of a photosensitizer chromophore is included in the mixture.

3. The method of claim 2, wherein the photosensitizer chromophore is a porphyrin, chlorin, bacteriochlorin, purpurin, phthalocyanine, naphthalocyanine, merocyanines, carbocyanine, texaphyrin, or non-tetrapyrrole.

4. The method of claim 2, wherein the photosensitizer chromophore is fluorescein, eosin, bodipy, nitro-benzo-diazol (NBD), erythrosine, acridine orange, doxorubicin, rhodamine 123, or picoerythrin.

5. The method of claim 1, wherein the inactivated virus exhibits substantially no infectivity.

6. A method of inactivating an *Ebola* virus, comprising the steps (a) contacting an *Ebola* virus with an effective amount of 1,5-iodonaphthyl azide; to form a mixture of the *Ebola* virus and the 1,5-iodonaphthyl azide, and (b) exposing the mixture to ultraviolet light for a time sufficient to inactivate the *Ebola* virus.

7. The method of claim 6, wherein an effective amount of a photosensitizer chromophore is included in the mixture.

8. The method of claim 7, wherein the photosensitizer chromophore is a porphyrin, chlorin, bacteriochlorin, purpurin, phthalocyanine, naphthalocyanine, merocyanines, carbocyanine, texaphyrin, or non-tetrapyrrole.

9. The method of claim 7, wherein the photosensitizer chromophore is fluorescein, eosin, bodipy, nitro-benzo-diazol (NBD), erythrosine, acridine orange, doxorubicin, rhodamine 123, or picoerythrin.

10. The method of claim 6, wherein the inactivated virus exhibits substantially no infectivity.

* * * * *